US007713537B2

(12) United States Patent
Arther et al.

(10) Patent No.: US 7,713,537 B2
(45) Date of Patent: May 11, 2010

(54) INSECT CONTROL DEVICE FOR PROLONGED TREATMENT OF ANIMALS CONTAINING COUMAPHOS AND DIAZINON

(75) Inventors: Robert G. Arther, Leawood, KS (US); Robert G. Pennington, Rayville, MO (US)

(73) Assignee: Bayer Healthcare LLC, Tarrytown, NY (US)

( * ) Notice: Subject to any disclaimer, the term of this patent is extended or adjusted under 35 U.S.C. 154(b) by 761 days.

(21) Appl. No.: 10/485,670

(22) PCT Filed: Aug. 28, 2002

(86) PCT No.: PCT/US02/27324

§ 371 (c)(1),
(2), (4) Date: Feb. 2, 2004

(87) PCT Pub. No.: WO03/020020

PCT Pub. Date: Mar. 13, 2003

(65) Prior Publication Data

US 2004/0202690 A1 Oct. 14, 2004

Related U.S. Application Data

(60) Provisional application No. 60/315,406, filed on Aug. 28, 2001.

(51) Int. Cl.
*A01N 25/34* (2006.01)

(52) U.S. Cl. .............. 424/411; 424/405; 424/409; 119/653

(58) Field of Classification Search .................. None
See application file for complete search history.

(56) References Cited

U.S. PATENT DOCUMENTS

| 4,562,794 | A | 1/1986 | Speckman |
| 4,674,445 | A | 6/1987 | Cannelongo |
| 4,879,117 | A | 11/1989 | Rombi ..................... 424/411 |
| 5,018,481 | A | 5/1991 | Rose et al. |
| 5,104,659 | A * | 4/1992 | Fishbein et al. ............ 424/411 |
| 5,194,265 | A | 3/1993 | Boettcher et al. .......... 424/411 |
| 5,472,955 | A | 12/1995 | Kellerby ..................... 514/86 |
| 6,232,328 | B1 | 5/2001 | Dorn et al. .................. 514/341 |
| 2008/0115737 | A1* | 5/2008 | Arther et al. ............... 119/650 |

FOREIGN PATENT DOCUMENTS

EP 0400438 5/1990

* cited by examiner

*Primary Examiner*—Neil Levy

(57) ABSTRACT

Annoying insects are controlled by attaching an insect control device to the body of the animal to be treated. The insect control device is a molded article, preferably in the form of an ear tag, which has been formed from a powder mixture of coumaphos and diazinon, polyvinyl chloride, and a plasticizer. The coumaphos and diazinon are generally used in an amount that would prolong the insecticidal activity without detracting from the suitability of the device.

9 Claims, No Drawings

INSECT CONTROL DEVICE FOR PROLONGED TREATMENT OF ANIMALS CONTAINING COUMAPHOS AND DIAZINON

This application claims benefit of U.S. Provisional Application Ser. No. 60/315,406, filed Aug. 28, 2001, the contents of which are incorporated herein by reference in their entirety.

FIELD OF THE INVENTION

The present invention relates to an improved insect control device for animals especially livestock, a method of making the devices, and a process for protecting livestock against insects for a prolonged period.

BACKGROUND OF THE INVENTION

Livestock are frequently troubled by various types of insects such as flies and lice that transmit infection of the skin, eyes, and ears as well as cause irritation leading to loss of production. Several approaches have been taken to alleviate this insect problem. One approach requires application of an insecticide spray on the livestock. This approach is undesirable because it requires a substantial amount of time and labor to gather and treat the livestock. Furthermore, this approach is effective for only a short period and requires frequent applications. A more economical and less labor-intensive approach is, therefore, generally preferred.

Another approach is the application of insecticide by contacting the target livestock with a device from which an insecticide is dispensed. Dispensers such as dust bags or oilers are placed in areas where it is anticipated that the livestock will come into contact with them. While this approach reduces the amount of labor involved in treating livestock, it does not ensure that each animal will receive the necessary treatment at regular intervals.

Yet another approach employs slow release pesticide mixed with a resinous substance that will release the insecticide over an extended period of time. These pesticide-containing resins have been used in a variety of forms ranging from collars to tags that are attached to various body parts of the animal. The use of pesticide-containing ear tags is of particular interest for treating livestock as is evident from the number of patents directed to such ear tags.

For example, U.S. Pat. Nos. 4,366,777 and 4,562,794 disclose ear tags in which a liquid insecticide dispenser is used. In U.S. Pat. No. 4,366,777, the liquid insecticide is enclosed in a fibrous or foam reservoir wicked onto the surface of the tag. In U.S. Pat. No. 4,562,794, the dispenser or reservoir containing the insecticide is attached to an animal identification tag. Release of the insecticide is dependent upon migration or diffusion of the insecticide through a semi-permeable membrane.

U.S. Pat. No. 4,428,327 discloses an insecticide-impregnated tape that is attached to a conventional ear tag. Each of these tags has been found to be disadvantageous because the insecticide containing reservoir or tape may be detached from the tag by fences or brush. It would, therefore, be advantageous to have a tag in which the insecticide is directly incorporated.

Such an approach is disclosed in U.S. Pat. Nos. 4,721,064; 4,195,075; and 4,265,876 as well as in Miller et al., ("Release of Pyrethroids from Insecticidal Ear Tags," J. Econ. Entomol. 76:1335-1340, 1983) and Miller et al., ("Release Rates from Cattle Insecticidal Ear Tags in Various Regions of the United States," The Southwestern Entomologist, Vol. II(1), pages 45-50, March 1986). The Miller et al. disclosures and U.S. Pat. No. 4,195,075 are, however, limited to liquid insecticides which can evaporate at ambient temperatures. Use of such liquid insecticides may be undesirable in areas where the ambient temperature is high enough to cause rapid evaporation of the insecticide and thus, result in an undesirably greater release of insecticide over a shorter period of time.

More specifically, U.S. Pat. No. 4,265,876 is limited to tags containing pyrethroid insecticides whereas coumaphos is not a pyrethroid. U.S. Pat. No. 5,018,481 discloses an insect control device, attachable to the body of a target animal, that has been formed from a powder mixture of coumaphos, polyvinyl chloride, and a plasticizer. The coumaphos is used in an amount of 5 to 30% of the device.

In order for the device to have a prolonged use of about four or more months of effective control of insects especially on cattle, a large concentration of insecticide must be incorporated into the carrier. If too much insecticide is used in plastic molded carriers, for example, in the form of ear tags, they become unsuitably soft. By the present invention, there is provided a suitable device for providing prolonged and effective insecticidal activity.

SUMMARY OF THE INVENTION

In accordance with the foregoing, the invention encompasses an insect control device for livestock which effectively releases insect controlling agent for a period of about four or more months. That is, a sufficient quantity of insect controlling agent is released to provide efficacious control of insects. In its present embodiment, the device is in the form of an ear tag comprising a molded article formed from a mixture of an effective combination of the active ingredients, coumaphos and diazinon, polyvinyl chloride, and a plasticizer. By an effective combination is meant that the coumaphos and diazinon are employed in an amount sufficient to provide insecticidal activity. To be sure, while coumaphos and diazinon are known as insecticides, it has been surprising to obtain results of prolonged treatment with a device containing the combination of solid coumaphos with liquid diazinon in accordance with this invention. An amount of about 10 to about 60 percent by weight and preferably about 25 to about 40 percent by weight of the active ingredients based on the total weight of the device may be employed. Of this amount about 10 to about 30 percent by weight and preferably about 20 to about 25 percent by weight may be coumaphos, and about 10 to about 30 percent by weight and preferably about 20 to about 25 percent by weight may be diazinon.

The active ingredients may be incorporated into any compatible material which can carry the active ingredients at high loads without being rendered unsuitable in their handling or performance in the service environment. Moreover, the material should be such as would releasably contain the active ingredients. The phrase "releasably contain" means that the active ingredient, while in the compatible material, is disposed to contact an insect that comes into contact therewith.

In one embodiment, the present invention encompasses a suitable ear tag having a high concentration of insecticide that is effective for about four or more months. By the term "suitable" is meant that the material of the device retains its integrity as to handling or performance in the service environment. Illustratively, a plastic molded ear tag does not become tacky and continues to release insecticides for a prolonged period.

DETAILED DESCRIPTION OF THE INVENTION

As set forth above, the insect control devices of the present invention are formed from a mixture of an effective combination coumaphos and diazinon, polyvinyl chloride, and a plasticizer. Coumaphos is a solid organophosphorous insecticide which is effective against arthropods including flies, grubs, lice, ticks, and mites. In the devices of the present invention, coumaphos is generally present in an amount of from about 3 to about 30 wt % of the total weight of the device, preferably in an amount of from about 10 to about 25 wt %, and most preferably in an amount of from about 10 to about 15 wt %. Diazinon is a liquid organophosphorous insecticide which is also effective against arthropods including flies, grubs, lice, ticks, and mites. In the devices of the present invention, diazinon is present in an amount of about 10 to about 30% by weight and preferably about 20 to about 25% by weight based on the total weight of 10 to 20 g.

It is, of course, possible to include other known insecticides in the mixture from which the insect control devices of the present invention are formed. The other known insecticides should be such as would not detract from the insecticidal activity or detract from the suitability of the device.

Polyvinyl chloride is generally present in the devices of the present invention in an amount of from about 30 to about 70 wt % of the total weight of the device, preferably in an amount of from about 40 to about 60 wt %, and most preferably from about 45 to about 55 wt %.

The plasticizer used in making the insect control devices of the present invention may be any of the known plasticizers. Specific examples of suitable plasticizers include: phthalates such as dioctyl phthalate, diphenyl dimethyl phthalate, and dihexyl phthalate; sebacates such as dipentyl sebacate, n-butyl benzyl sebacate, and dibenzyl sebacate; adipates such as dioctyl adipate, dicapryl adipate, di-isobutyl adipate, and dinonyl adipate; hydrogenated polyphenols; alkylated aromatic hydrocarbons; and polyester plasticizers such as polyesters of polyols and polycarboxylic acids having a molecular weight of at least 2000. The plasticizer is present in an amount of from 0 to about 30 wt % of the total weight of the insect control device, preferably from about 5 to about 25 wt %, and most preferably from about 10 to about 25 wt %.

Other materials such as dyes, pigments, lubricants, lakes, fillers, anti-oxidants, and ultraviolet stabilizers may optionally be included in the mixture from which the insect control devices of the present invention are formed. If these materials are included, they are generally present in an amount of from about 1 to about 10 wt %, preferably in an amount of from about 2 to about 4 wt %.

In a method for preparing the device, the solid coumaphos and liquid diazinon are incorporated as follows. The polyvinyl chloride and plasticizer are mixed together and heated to a temperature of about 180° F. The diazinon is then added and the mixture is blended for 3 hours. The mixture is then allowed to cool to 68 to 80° F. (ideal 72° F.). The coumaphos and other ingredients are then added and blended for 2 hours. The mixture containing coumaphos, diazinon, polyvinyl chloride, plasticizer and optional ingredients is a mixture of solids which is molded, preferably by injection molding, to the desired form. The preferred form is an ear tag which may be attached directly to the ear of livestock. Techniques for molding such mixtures are known to those skilled in the art. One such molding method is disclosed in U.S. Pat. No. 4,195, 075. Techniques for attaching the molded insect control device to an animal, such as livestock, are also well known in the art. As used herein, the term "livestock" is intended to include cattle, sheep, pigs, horses, and other animals.

EXAMPLES

The present invention is further illustrated by the following examples which should not be construed as limiting in any way.

Example 1

3712 g of polvinyl chloride and 119 g of acetyl tributyl citrate were combined and heated to 180° F. Technical diazinon (1907 g) was added to the mixture and blended for 3 hours. The mixture was allowed to cool for 8 hours: 1906 g of technical coumaphos and 95 g of titanium dioxide were added and mixed for 2 hours. Ear tags were produced by passing the mixture through an injection molding procedure at 250° F. to produce individual ear tags weighing 14-15 g containing 18.7% plasticizer, 20% coumaphos, and 20% diazinon.

Example 2

4234 g of polyvinyl chloride and 1389 g of acetyl tributyl citrate were combined and heated to 180° F. Technical diazinon (1906 g) was added to the mixture and blended for 3 hours. The mixture was allowed to cool for 8 hours: 1906 g of technical coumaphos and 95 g of titanium dioxide were added to the mixture and blended for 2 hours. Ear tags were produced by passing the mixture through an injection molding procedure at 250° F. to produce individual tags weighing 14-15 g containing 13.6% plasticizer, 20% coumaphos, and 20% diazinon.

Example 3

4667 g of polyvinyl chloride and 956 g of acetyl tributyl citrate were combined and heated to 180° F. Technical diazinon (1906 g) was added to the mixture and blended for 3 hours. The mixture was allowed to cool for 8 hours: 1906 g of coumaphos and 95 g of titanium dioxide were added and blended for 2 hours. Ear tags were produced by passing the mixture through an injection molding procedure at 250° F. to produce individual tags weighing 14-15 g containing 9.4% plasticizer, 20% coumaphos, and 20% diazinon.

Example 4

4878 g of polyvinyl chloride and 318 g of expoxidized soybean oil were combined and blended at approximately 180° F.: 2738 g of technical diazinon was added and blended for 3 hours. The mixture was cooled to 72° F.: 1500 g of coumaphos and 95 g of titanium dioxide were added and blended for 2 hours. Ear tags were produced by passing the mixture through an injection molding procedure at 250° F. to produce individual tags weighing 14-15 g containing 15% coumaphos and 25% diazinon.

Example 5

Determination of the Depletion Rate of Coumaphos+Diazinon from Cattle Ear Tags

The ear tags produced in Examples 1-3 were attached to the ears of cattle for a period of 20 weeks. Tags were removed from animals at pre-determined intervals, weighed, and analyzed to determine the quantity and release rate of active ingredient from the molded tags. The results are displayed below in Table 1.

TABLE 1

| Weeks After Application to Cattle | Depletion Rate of Active Ingredients (Coumaphos + Diazinon) From Ear Tags (mg/day) | | |
|---|---|---|---|
| | TAG A | TAG B | TAG C |
| 4 | 61.3 | 30.0 | 50.0 |
| 8 | 51.0 | 70.0 | 32.3 |
| 12 | 19.1 | 3.0 | 17.1 |
| 16 | 4.6 | 4.9 | 0 |
| 20 | 4.6 | 17.8 | 11.4 |

The results of this study demonstrate that coumaphos and diazinon are released together from the molded ear tags for at least 20 weeks after application to cattle. The greatest release rate was observed for the first 8 weeks after application.

Example 6

Determination of the Effectiveness of Coumaphos+Diazinon Ear Tags to Control Flies on Cattle The ear tags produced in Examples 1-3 were attached to the ears of cattle in herds located in Kentucky, Nebraska, and Missouri (one or two tags/animal). The mean number of horn flies (*Haematobia irditans*) and/or face flies (*Musca autumnalis*) per animal was determined prior to application of the ear tags. The cattle were observed at weekly intervals for up to 17 weeks after tags were applied and fly counts were performed. Percent efficacy was calculated by comparing the mean number of horn (or face) flies per animal on the ear tag treated herds with the mean number of flies on adjacent untreated cattle according to the following formula.

$$\text{Percent Efficacy} = \frac{\text{mean no. flies on untreated animals} - \text{mean no. flies on ear tag treated animals}}{\text{mean no. flies on untreated animals}} \times 100$$

The results are displayed below in Tables 2-4.

TABLE 2

| | Kentucky* | | | |
|---|---|---|---|---|
| | Horn Flies | | Face Flies | |
| | Mean No. Flies/ Animal | % Efficacy | Mean No. Flies/ Animal | % Efficacy |
| Pre-Treatment | 62.0 | — | 30.5 | — |
| Weeks Post-Treatment | | | | |
| 1 | 0 | 100 | 11.8 | 56.3 |
| 2 | 0 | 100 | 8.8 | 68.6 |
| 3 | 0 | 100 | 7.2 | 66.5 |
| 4 | 0 | 100 | 6.7 | 73.2 |
| 5 | 0 | 100 | 8.2 | 61.9 |

TABLE 2-continued

| | Kentucky* | | | |
|---|---|---|---|---|
| | Horn Flies | | Face Flies | |
| | Mean No. Flies/ Animal | % Efficacy | Mean No. Flies/ Animal | % Efficacy |
| 6 | 0 | 100 | 1.7 | 87.5 |
| 7 | 0 | 100 | 2.7 | 74.0 |
| 8 | 0 | 100 | 1.9 | 79.3 |
| 9 | 0 | 100 | 2.6 | 70.8 |
| 10 | 0 | 100 | 2.9 | 57.4 |
| 11 | 0 | 100 | 2.1 | 70.8 |
| 12 | 0 | 100 | 2.9 | 59.2 |
| 13 | 0 | 100 | 4.9 | 29.0 |
| 14 | 0 | 100 | 3.7 | 50.0 |
| 15 | 4 | 99.1 | 3.3 | 53.5 |

*two tags/animal

TABLE 3

| | Missouri* | | | |
|---|---|---|---|---|
| | Horn Flies | | Face Flies | |
| | Mean No. Flies/ Animal | % Efficacy | Mean No. Flies/ Animal | % Efficacy |
| Pre-treatment | 32.1 | — | 1.4 | — |
| Weeks Post-treatment | | | | |
| 1 | 1 | 99 | 0.5 | 81 |
| 2 | 0 | 100 | 0.4 | 90 |
| 3 | 0 | 100 | 2.8 | 84 |
| 4 | 0 | 100 | 9.7 | 45 |
| 5 | 0 | 100 | 4.6 | 75 |
| 6 | 0 | 100 | 3.1 | 84 |
| 7 | 0 | 100 | 5.2 | 57 |
| 8 | 0 | 100 | 4.1 | 87 |
| 9 | 0 | 100 | 6.4 | 82 |
| 10 | 0 | 100 | 10.3 | 61 |
| 11 | 0 | 100 | 15.9 | 50 |
| 12 | 2 | 99 | 14.6 | 55 |
| 13 | 5 | 99 | 21.5 | 37 |
| 14 | 75 | 85 | 24.0 | 0 |
| 15 | 77 | 84 | 23.0 | 22 |
| 16 | 75 | 72 | 21.2 | 5 |

*two tags/animal

TABLE 4

| | Nebraska* | |
|---|---|---|
| | Horn Flies | |
| | Mean No. Flies/ Animal | % Efficacy |
| Pre-treatment | 248 | — |
| Weeks Post-treatment | | |
| 1 | — | — |
| 2 | 36 | 86 |
| 3 | 49 | 87 |
| 4 | 40 | 93 |
| 5 | 32 | 94 |
| 6 | 105 | 79 |
| 7 | 49 | 92 |

TABLE 4-continued

Nebraska*

Horn Flies

| | Mean No. Flies/Animal | % Efficacy |
|---|---|---|
| 8 | 41 | 95 |
| 9 | 62 | 87 |
| 10 | 57 | 90 |
| 11 | 58 | 91 |
| 12 | 69 | 90 |
| 13 | 119 | 81 |
| 14 | 385 | 38 |
| 15 | 234 | 45 |
| 16 | 420 | 26 |
| 17 | 61 | 52 |

*one tag/animal

The results of these studies demonstrated that coumaphos and diazinon are depleted from the ear tag devices described in Examples 1-3 at sufficient quantity to provide efficacious control of horn and face flies on cattle for at least 17 weeks.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An ear tag which effectively releases insect controlling agents for a period of about four months comprising a molded article formed from a mixture of coumaphos and diazinon, polyvinyl chloride, and a plasticizer, wherein coumaphos is present in an amount of from about 15 to about 25 wt % of the total device, diazinon is present in an amount of from about 20 to about 29 wt % of the total weight of the device, the polyvinyl chloride is present in an amount of from about 40 to about 60 wt % of the total weight of the device, and the plasticizer is present in an amount of from about 5 to about 25 wt % of the total weight of the device.

2. An insect control device for attachment to animals which effectively releases insect controlling agents for a period of about four months comprising a molded article formed from a mixture of coumaphos and diazinon, polyvinyl chloride, and a plasticizer, wherein coumaphos is present in an amount of about 20 wt % of the total device, diazinon is present in an amount of about 20 wt % of the total weight of the device, the polyvinyl chloride is present in an amount of from about 40 to about 60 wt % of the total weight of the device, and the plasticizer is present in an amount of from about 5 to about 25 wt % of the total weight of the device.

3. The device of claim 2, wherein the article is in the form of an ear tag.

4. The device of claim 2, wherein the plasticizer is selected from the group consisting of phthalates, sebacates, adipates, hydrogenated polyphenols, alkylated aromatic hydrocarbons, and polyesters.

5. The device of claim 2, wherein the mixture to be molded also includes up to about 5 wt % stabilizer.

6. The device of claim 5, wherein the mixture to be molded also includes up to about 5 wt % pigment or lake.

7. The device of claim 6, wherein the article is in the form of an ear tag.

8. A process for treating livestock to control insects comprising the step of attaching the device of claim 1 to an ear of an animal to be treated.

9. The process of claim 8, wherein livestock include cattle, sheep, pigs, and horses.

* * * * *